(12) United States Patent
Lulla et al.

(10) Patent No.: US 7,404,400 B2
(45) Date of Patent: Jul. 29, 2008

(54) SPACER DEVICE FOR INHALER

(75) Inventors: Amar Lulla, Mumbai (IN); Xerxes Rao, Bombay (IN)

(73) Assignee: Cipla Limited, Mumbai (IN)

( * ) Notice: Subject to any disclaimer, the term of this patent is extended or adjusted under 35 U.S.C. 154(b) by 533 days.

(21) Appl. No.: 10/617,850

(22) Filed: Jul. 14, 2003

(65) Prior Publication Data

US 2004/0094148 A1 May 20, 2004

Related U.S. Application Data

(63) Continuation of application No. 09/857,707, filed as application No. PCT/GB99/00834 on Mar. 18, 1999, now abandoned.

(51) Int. Cl.
*A61M 11/00* (2006.01)

(52) U.S. Cl. ............... 128/200.14; 128/200.22; 128/200.23; 128/203.12

(58) Field of Classification Search ........... 128/200.14, 128/200.22, 200.23, 203.12, 204.11, 204.12
See application file for complete search history.

(56) References Cited

U.S. PATENT DOCUMENTS

| | | | | |
|---|---|---|---|---|
| 4,206,758 A | * | 6/1980 | Hallworth et al. | 128/203.15 |
| 4,509,515 A | * | 4/1985 | Altounyan et al. | 128/200.23 |
| 5,165,391 A | | 11/1992 | Chiesi et al. | |
| 5,178,138 A | | 1/1993 | Walstrom et al. | |
| 5,318,016 A | | 6/1994 | Mecikalski | |
| 5,477,849 A | | 12/1995 | Fry | |
| 5,676,130 A | | 10/1997 | Gupte et al. | |
| 5,816,240 A | | 10/1998 | Komesaroff | |
| 5,875,776 A | | 3/1999 | Vaghefi | |
| 6,030,363 A | * | 2/2000 | Kriesel | 604/132 |
| 6,039,042 A | | 3/2000 | Sladek | |
| 6,095,141 A | * | 8/2000 | Armer et al. | 128/204.26 |
| 6,257,231 B1 | | 7/2001 | Shick et al. | |
| 6,435,176 B1 | * | 8/2002 | Berg et al. | 128/200.23 |
| 2002/0026935 A1 | * | 3/2002 | Schmidt et al. | 128/200.14 |

FOREIGN PATENT DOCUMENTS

| | | | |
|---|---|---|---|
| GB | 2110543 | | 6/1993 |
| GB | 2299512 | | 10/1996 |
| GB | 2299512 A | * | 10/1996 |
| WO | 9100117 | | 1/1991 |
| WO | 9311817 | | 6/1993 |
| WO | WO 93/11817 | * | 6/1993 |
| WO | 9712639 | | 4/1997 |
| WO | WO 98/19727 | * | 5/1998 |

* cited by examiner

*Primary Examiner*—Patricia Bianco
*Assistant Examiner*—Nihir Patel
(74) *Attorney, Agent, or Firm*—Stevens, Davis, Miller & Mosher LLP

(57) ABSTRACT

A spacer device for an inhaler is made of a non-metallic antistatic material, preferably polyamide. The device may comprise two frustoconical members joined at their wider ends, with an inlet and outlet at, respectively, the two narrower ends. A measured dose of medicament is injected through the inlet, and then inhaled from the chamber through the outlet.

10 Claims, 1 Drawing Sheet

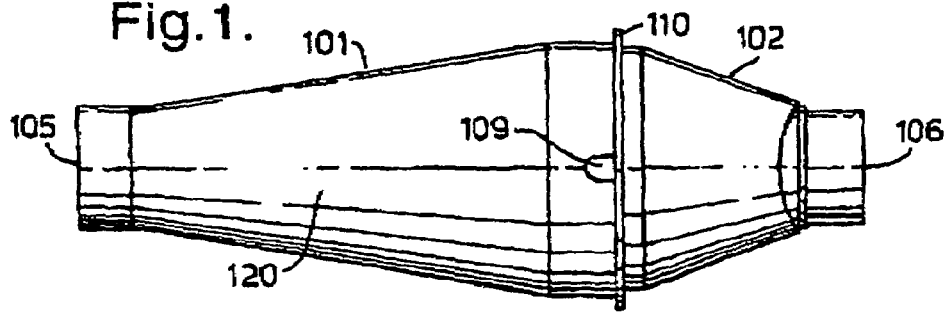
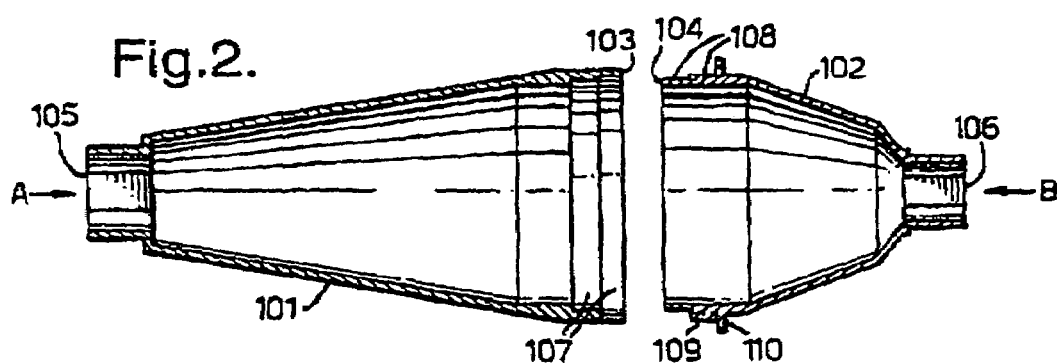
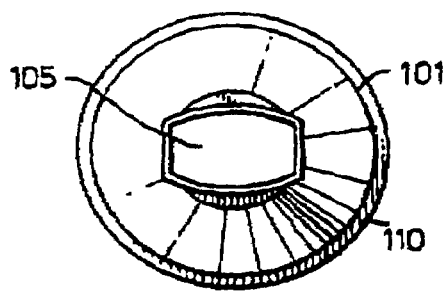
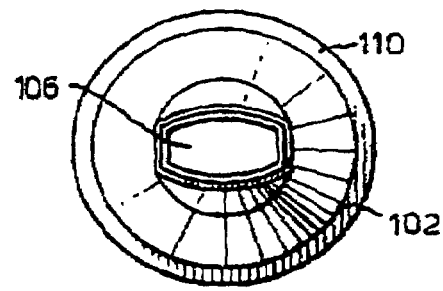
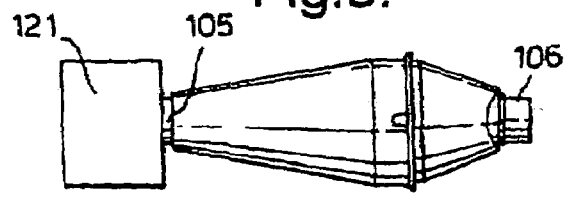

SPACER DEVICE FOR INHALER

This application is a continuation application of U.S. Ser. No. 09/857,707, filed Oct. 10, 2001, which, in turn, is a §371 Application of International Application No. PCT/GB99/00834, filed on Mar. 18, 1999, claiming the priority of South African Application No. 98/11257, filed Dec. 9, 1998, the entire disclosures of which are incorporated herein by reference in their entireties.

The invention relates to a spacer device for an inhaler for oral administration of a medicament by inhalation.

There are essentially two known types of inhaler in common use. In the fist type, a jet of gas having the dose of medicament therein is produced and is inhaler is used by directing the jet into the throat whilst inhaling. The gas is usually an aerosol propellant and the medicament is a fine powder. Whilst thee inhalers are excellent at delivering predetermined doses of medicament, there is a tendency for the powder to be deposited in the mouth and throat of the user, and thus not reach the lungs. Indeed, really successful use of these inhalers requires not only practice but good coordination between a patient's breathing and actuation of the device. The efficiency of administration by this route also depends on the shape and dimensions of the patient's oral cavity.

The second type of inhaler is essentially simpler and essentially comprises a dose of powdered medicament which is withdrawn from the device suspended in air by the patient inhaling through the device. A drawback of these devices is the variability of the inhalation air flow which, in turn affect the carry of powder from the device and the velocity of inhalation. Powder deposit in the mouth and throat is common until the patient is well-practised in use of the device.

With a view to reducing these problems, it has been proposed to provide a spacer device between the medicament source and the mouth of the patient. The spacer device essentially comprises a chamber with an inlet for receiving the medicament suspended in gas (eg. air or propellant), and an outlet through which the medicament suspension is drawn by inhalation of the patient The use of a spacer device improves the efficiency of inhalation of the medicament into the lungs.

Spacer devices are known which are made of metal or of polycarbonate. Metal devices are not preferred and polycarbonate devices are the more common. We have found, however, that there is a drawback with polycarbonate devices in that the powdered medicament becomes deposited on the inner walls of the chamber, thus reducing the dose inhaled by the patient. We have investigated this phenomenon and have found that a similar effect is shown when a spacer is made of various other plastics materials including polypropylene, polystyrene and low density polyethylene. Further, we have found that whilst this problem can be reduced by including an antistatic agent in the plastics material, the improvement is only short-term: the antic effect of the agent soon wears off.

We have now found that this problem can be overcome by using a non-metallic material for the spacer device, which is inherently substantially antistatic. We have found that, surprisingly, there are such plastics materials from which spacer devices can be made. We have found, in particular, that plastics materials which absorb and retain moisture are especially suitable. Among the most preferred materials are the polyamides: routine trial and experiment will reveal whether or not any particular material is useful.

Accordingly, in one aspect the invention provides a spacer device for the oral administration of a volatile medium containing a medicament, which device comprises a chamber having an inlet to admit a measured dose of medicament and an outlet to be received in the mouth, wherein the chamber is made of a non-metallic antistatic material.

In another aspect, the invention provides an inhaler for dispensing a measured dose of a medicament in a volatile medium, a spacer device for receiving the medium, and means whereby the user can inhale the said medium from the spacer device, wherein the spacer device is made of a non-metallic substantially antistatic material.

The invention also includes the use of a non-metallic antistatic spacer device for the inhalation of a particulate medicament in a volatile medium.

The invention firer includes a method of administering a dose of a fine particulate medicament suspended in a gas, which comprises injecting said dose into a non-metallic antistatic chamber, and inhaling the dose from the chamber.

The spacer devices of the invention can be of various shapes and constructions but we prefer the chamber to comprise two frustoconical members assembled together coaxially at their divergent ends, said inlet and outlet being respectively at the opposed convergent ends. Preferably, the divergent end of one member is received in the divergent end of the other member to provide a substantially air-tight seal. Preferably also the divergent end have complementary stepped surfaces to provide a close air-tight fit. Locking me can be provided to lock the two members together in the assembled condition.

In order that the invention may be more fully understood, one embodiment of spacer device of the invention will now be described, by way of example only, with reference to the accompanying drawings, wherein:

FIG. 1 is a plan view of the assembled spacer device embodiment according to the present invention;

FIG. 2 is a longitudinal axial sectional view of the spacer device, the cones being dismantled;

FIG. 3 is an end view in direction A of FIG. 2;

FIG. 4 is an end view in direction B of FIG. 2; and

FIG. 5 is a schematic illustration of the spacer device positioned on a medicament container (eg. pump).

Referring to the FIGS., 101 and 102 are two conical members made of anti-static material defining chamber 120. The conical members 101 and 102 are assembled at their divergent ends, 103 and 104, respectively. The convergent end 105 of the conical member 101 is an inlet and is adapted to connect with a pumping device (not shown) containing the medicinal composition. The convergent end 106 of the conical member 102 is the outlet and is adapted to be inserted into the mouth of a patient. The inner surface at the divergent end of the conical member 101 is provided with stepped rings 107, the steps being directed towards the diverging end, and the outer surface at the divergent end of the conical member 102 being provided with stepped rings 108 corresponding to the stepped rings 107. A stop 110 at the divergent end of the conical member 102 restricts insertion of the conical member 101. The conical members 101 and 102 are provided with locking mean 109, such as a notch and the projection to ensure that the two members have been properly assembled.

In use, inlet 105 is connected to an aerosol medicament reservoir (121) for example, and a dose of inhalant suspension is pumped into chamber 120. The patient then places outlet 106 in the mouth and inhales steadily to draw the suspension into the lungs.

A polyamide spacer of the invention was compared with various commercially available polycarbonate and metallic spacers using the fine particles assessment test (Aerodynamic assessment of fine particle fraction as per BP Addendum 1996 using apparatus A and ten doses).

This test for fine particle assessment by twin impinger gives an in vitro estimate of the distribution of the drug in the human respiratory tract. The apparatus comprises two parts. The first part is an upper impingement chamber which corresponds to the oropharyngeal cavity (Stage 1) and has a nominal particle size cut-off of 6.4 μm. The drug deposited here is regarded as non-respirable since it corresponds to drug deposited in the mouth or the throat. The second part is a lower impingement chamber (Stage 2) which corresponds to the lungs. The amount of drug deposited here of particle size less than 6.4 micron, corresponds to the amount of drug which would be available immediately at the site of action i.e. in the lungs, and is considered to be the respirable fraction.

The test was conducted using a Budecourt 100 inhaler at 100 mcg dose, fitted with a series of different spacers. The spacer according to the invention was as illustrated in the drawings hereof and was made of polyamide. The results were as follows:

| Retention in | Spacer of invention | A Ektar | B polycarbonate | C metal | D polycarbonate (composition) |
|---|---|---|---|---|---|
| | | | Prior art spacers | | |
| Actuator | 15.06 | 13.92 | 10.13 | 18.73 | 8.91 |
| Spacer | 16.66 | 59.64 | 45.95 | 26.52 | 49.01 |
| Stage 1 | 8.87 | 9.14 | 8.33 | 13.14 | 6.44 |
| Stage 2 | 59.41 | 17.30 | 35.59 | 41.61 | 35.64 |

The numbers are the percent by weight of particulate deposited after ten "inhalations".

The results show the advantages of the spacer of the invention both as to the much lower deposition of solids in the spacer itself and the much higher deposit in Stage 2.

The invention claimed is:

1. A spacer device for the oral administration of a volatile medium containing a medicament, which device comprises a chamber having an inlet to admit a measured dose of medicament and an outlet to be received in the mouth, wherein the chamber is made of a polyamide and comprises two frustoconical members assembled together coaxially at divergent ends, said inlet and outlet being respectively at opposed convergent ends.

2. A device according to claim 1, wherein the divergent end of one member is received in the divergent end of the other member to provide a substantially air-tight seal.

3. A device according to claim 2, wherein the said divergent ends have complementary stepped surfaces to provide a close air-tight fit.

4. A spacer device, for the oral administration of a volatile medium containing a medicament. which device comprises a chamber having an inlet to admit a measured dose of medicament and an outlet to be received in the mouth, wherein the chamber is made of a polyamide and comprises two frustoconical members assembled together coaxiallv at diver2ent ends, said inlet and outlet beina respectively at opposed convergent ends, wherein locking means are provided to lock the two members together in assembled condition.

5. An inhaler for dispensing a measured dose of a medicament in a volatile medium, a spacer device for receiving the medium, and means whereby the user can inhale the said medium from the spacer device, wherein the spacer device is made of polyamide and comprises two frustoconical members assembled together coaxially at their divergent ends, said inlet and outlet being respectively at the opposed convergent ends.

6. An inhaler and spacer device according to claim 5, wherein the spacer device is for the oral administration of a volatile medium contain medicament, which device comprises a chamber having an inlet to admit a measured dose of medicament and an outlet to be received in the mouth.

7. The use of a non-metallic antistatic spacer device according to claim 1, for the inhalation of a particulate medicament in a volatile medium.

8. The use according to claim 7, wherein there is substantially little or no deposit of medicament on the inside of the device.

9. A method of administering a dose of a fine particulate medicament suspended in a gas, which comprises injecting said dose into a polyamide chamber, the chamber comprising two frustoconical members assembled together coaxially at their divergent ends, said inlet and outlet being respectively at the opposed convergent ends, and inhaling the dose from the chamber.

10. A method according to claim 9, wherein the chamber device is in a device having an inlet to admit a measured dose of medicament and an outlet to be received in the mouth.

* * * * *